July 30, 1935. C. C. MALLERIN Plant Pat. 129
ROSE
Filed Feb. 16, 1935
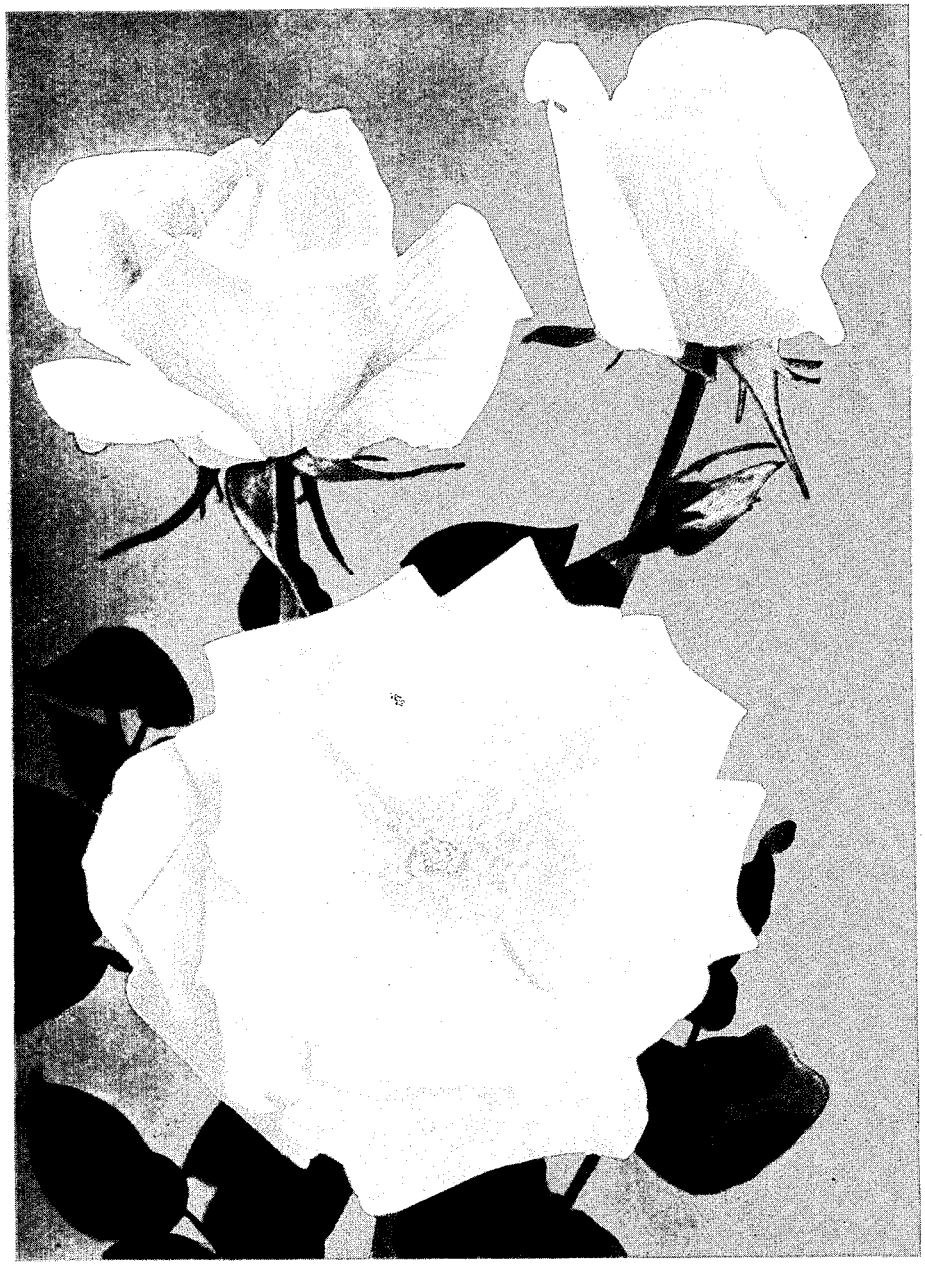
Inventor
Charles C. Mallerin
By Robb & Robb
attorneys Patented July 30, 1935

Plant Pat. 129

UNITED STATES PATENT OFFICE

129

ROSE

Charles C. Mallerin, Varces, France, assignor to
The Conard-Pyle Company, West Grove, Pa.

Application February 16, 1935, Serial No. 6,905

1 Claim. (Cl. 47—61)

The present invention relates to a new and distinct variety of rose, the result of a definite breeding in an effort to produce a better rose of the distinct coloring herein disclosed.

To produce this rose with the desired characteristics as to habits and growth, I crossed the hybrid tea roses, Mrs. Pierre S. du Pont and Cecile Walter, the former being used as the female and the latter as the male or pollen parent, with the result that the new variety is characterized as to novelty by its having longer buds and larger flowers, retaining their color longer and with more pleasing fragrance, and producing more flowers than any existing rose of the color, generally speaking.

This new variety has been asexually reproduced and its characteristics appear fixed permanently. Observations show that it has inherited the best characteristics of its respective parents, that is, the healthy foliage and free flowering of Mrs. Pierre S. du Pont and the strong growth, fine form and beautiful general color of Cecile Walter, with its own distinctive characteristic shading.

It will be noted hereinafter that the color of the open flower is the same as the bud, except as this may be softened to a golden flush. This color is retained comparatively long for a rose of this type. As it ages the color changes to a soft satiny pink with attractive tints but does not lose any of its loveliness, clearness or refreshing characteristics.

The following is a detailed description of this rose plant and its flower, observations relative thereto having been made in connection with plants as growing in the field in the vicinity of West Grove, Pennsylvania, U. S. A., during the season of 1933 and 1934.

Parentage:—

*Seed parent.*—Mrs. Pierre S. du Pont.

*Pollen parent.*—Cecile Walter.

Classification:—

Hybrid tea.

*Flower*

(All color names refere to Ridgway's chart.)

Blooming habit:—

*Recurrent.*—Continuous.

Bud:—

*Size.*—Large.

*Form.*—Long, tapering.

*Color.*—Coral pink.

*Sepals.*—Branched, pointed ends.

*Calyx.*—Medium size, goblet shaped.

*Peduncle.*—Medium length, limber, hairy; color, olive green.

*Opening.*—Opens perfectly; unaffected by weather conditions.

Bloom:—

*Size.*—Large, 4½ to 5 inches.

*Borne.*—Sometimes singly, usually in clusters.

*Stems.*—Medium.

*Form.*—Loose; ends of some petals fold back, others the sides curl; petaloids curl over center. A very informal flower.

*Permanence.*—Lasts well for a flower of this type.

*Petalage.*—Varies; single flowers have from 25 to 40 petals; those from a cluster 15 to 25.

*Color.*—Coral pink overspread with a golden flush which is very heavy on lower half of petals; petals have an opalescent lustre which gives them a satiny appearance.

*Texture.*—Heavy, fairly leathery.

*Appearance.*—Satiny both inside and out.

*Form.*—Pear shaped.

*Arrangement.*—Loosely formed.

*Persistence.*—Drop off cleanly.

*Fragrance.*—Rich, honey.

*Lasting quality.*—Lasts until petals fall.

Genital organs:—

*Stamens, anthers.*—Numerous; color yellow.

*Stamens, filaments (threads).*—Long, color yellow.

Color:—

*Pollen.*—Yellow.

*Styles.*—Bunched, uneven length, short, slender.

*Stigmas.*—Flesh colored.

*Ovaries.*—Normal.

Fruit:—

*Form.*—Goblet shaped.

*Aspect.*—Seeds extending slightly above calyx rim.

*Sepals.*—Fold back.

*Plant*

Form:—

Bush.

Growth:—

Vigorous, branching.

Foliage:—

Leaves, compound of 5 leaflets; ribs and veins ordinary.

*Size.*—Medium.

*Quantity.*—Average.

*Color.*—New foliage, upper side slightly bronzy green; underside pale green. Mature foliage, upper side dark green; underside, olive green.

*Shape.*—Oval, pointed tips.

*Texture.*—Heavy, leathery.

*Edge.*—Serrated.

*Serrations.*—Shallow.

*Leaf stem.*—New, reddish; mature, green; hooked prickles on underside.

*Stipules.*—Very narrow, pointed, edges bearded.

*Disease resistance.*—Very good.

Wood:—

*New wood.*—Light green with occasional reddish stains; smooth.

*Old wood.*—Light green, rough.

Thorns:—

*Quantity.*—Fairly numerous but not excessive.

*Form.*—Straight along top line but slant back 45 degrees.

*Color when young.*—Pink.

*Position.*—Irregular.

*Short needles.*—Numerous on some canes; missing on others.

*Comparison*

In comparison with the rose Los Angeles, the nearest to it in flower of any well-known rose, the present plant is much more vigorous, disease-resistant, prolific-blooming and easier to grow.

I claim:

The new and distinct variety of rose plant, characterized by the long form of its bud, the distinctive coloring and size of its flower, as shown, the persistence of the color before change, and the great productivity and pleasing fragrance of said flower, as described.

CHARLES C. MALLERIN.